(12) United States Patent
Lopez et al.

(10) Patent No.: US 6,641,992 B2
(45) Date of Patent: Nov. 4, 2003

(54) AQUEOUS SOLUTION FOR PRESERVING TISSUES AND ORGANS

(75) Inventors: Georges Antoine Lopez, Craponne (FR); Silvina Ramella Virieux, Lyons (FR)

(73) Assignee: Cair L.G.L., Civrieux d'Azergues (FR)

( * ) Notice: Subject to any disclaimer, the term of this patent is extended or adjusted under 35 U.S.C. 154(b) by 0 days.

(21) Appl. No.: 09/988,936

(22) Filed: Nov. 19, 2001

(65) Prior Publication Data

US 2002/0068265 A1 Jun. 6, 2002

Related U.S. Application Data

(63) Continuation of application No. PCT/FR00/01336, filed on May 18, 2000.

(51) Int. Cl.[7] .................................................. C12N 5/00

(52) U.S. Cl. .............................. 435/1.3; 435/2; 435/325; 435/374; 436/18

(58) Field of Search .............................. 435/1.3, 2, 325, 435/374; 436/18

(56) References Cited

U.S. PATENT DOCUMENTS

| 4,798,824 | A | * | 1/1989 | Belzer et al. |
| 4,938,961 | A | * | 7/1990 | Collins et al. |
| 5,002,965 | A | * | 3/1991 | Ramwell et al. |
| 5,145,771 | A | * | 9/1992 | Lemasters et al. |
| 5,696,152 | A | * | 12/1997 | Southard |
| 6,321,909 | B1 | * | 11/2001 | Wicomb et al. |

* cited by examiner

Primary Examiner—Leon B. Lankford, Jr.
(74) Attorney, Agent, or Firm—Heslin Rothenberg Farley & Mesini P.C.; Mary Louise Gioeni, Esq.

(57) ABSTRACT

An aqueous solution for preserving tissues and organs and methods of use for the same are disclosed.

15 Claims, No Drawings

AQUEOUS SOLUTION FOR PRESERVING TISSUES AND ORGANS

FIELD OF THE INVENTION

This invention relates to an aqueous solution for preserving tissues and organs.

BACKGROUND OF THE INVENTION

After removal from a donor and before transplantation into a recipient, the organ(s) or tissues are subjected to an unavoidable period of ischemia. Thus the liquid solutions used to preserve the organ(s) and tissues have to:

wash the graft free of residual blood, cool down the organ, ensure effective prevention and protection against the lesions caused by ischemia.

The liquid solutions currently used do not ensure the preservation of all organs and tissues. Thus there exists a need for a single solution that preserves any tissue and organ.

The method generally used for preserving organs is static hypothermic preservation where the removed organ or tissue is rinsed with a cold preservation solution and maintained in the cold preservation solution. The problem with the cold preservation solutions currently available is that the organs or tissues are preserved for only a limited time, i.e. generally about 24 hours for the kidney, 12 to 18 hours for the liver, and 4 to 6 hours for the heart.

Further, the solutions used to preserve the organ(s) and tissues have different compositions according to the organ(s) and tissues that must be preserved.

For example, the solution EURO COLLINS marketed by FRESENIUS and the BELZER-VIASPAN liquid also known by the name UW (University of Wisconsin) marketed by DUPONT, are recommended for the preservation of the kidney. These solutions are so called "intracellular" type ionic mixtures, in which the potassium concentration is greater than the sodium concentration.

For hepatic preservation, the BELZER-VIASPAN solution may be used.

For cardiac graft preservation, the SAINT THOMAS solution may be used. This solution is a so called "extracellular"-type ionic mixture, in which the sodium concentration is greater than the potassium concentration. Further, this solution is free of any macromolecule. SAINT THOMAS is marketed by Laboratoires AGUETTANT.

The composition of EURO COLLINS, BELZER-VIASPAN, and SAINT THOMAS is set forth in Table 1 below.

TABLE 1

|  | SAINT-THOMAS | EURO COLLINS | BELZER |
| --- | --- | --- | --- |
| Sodium (mM) | 120 |  | 30 |
| Potassium (mM) | 16 |  | 125 |
| Raffinose (mM) |  |  | 30 |
| Lactobionate (mM) |  |  | 100 |
| Glutathione (mM) |  |  | 3 |
| Adenosine (mM) |  |  | 5 |
| Allopurinol (mg/l) |  |  | 1 |
| HEA (g/l) hydroxyethyl starch MW: 250 000 |  |  | 50 |
| $MgSO_4$ (mM) |  |  | 5 |

TABLE 1-continued

|  | SAINT-THOMAS | EURO COLLINS | BELZER |
| --- | --- | --- | --- |
| $H_2PO_4$ (mM) |  |  | 25 |
| $KH_2PO_4$ (g/l) |  | 2.0 |  |
| Glucose (g/l) |  | 25 |  |
| $HCO_3$ (mM) | 10 |  |  |
| Cl (mM) | 160 |  |  |
| Mg (mM) | 16 |  |  |
| $CaCl_2$ (mM) | 1.2 |  |  |
| $K_2HPO_4 3H_2O$ (g/l) |  | 9.70 |  |
| KCl (g/l) |  | 1.12 |  |
| $MgSO_4 7H_2O$ (g/l) |  | 7.38 |  |
| $NaHCO_3$ (g/l) |  | 0.86 |  |
| Osmolarity (mOsm/kg) | 290 | 320 | 300 |

As already stated and as shown in the summary table above, the solution selected for the cardiac preservation is of the extracellular type (rich in sodium), whereas the preservation solution for preserving the kidney and the liver is of the intracellular type (rich in potassium).

One of the disadvantages of these solutions is that they do not preserve all organs and tissues.

The subject invention relates to novel compositions and methods used to preserve a wider variety of organs and tissues for a longer time and in better functional condition than previously possible.

SUMMARY OF THE INVENTION

As used herein, the term "tissues" may include without limitation veins, arteries, valves, and vessels.

One aspect of the present invention relates to an aqueous solution for the preservation of tissues and organs comprising calcium ions, polyethylene glycol having a molecular weight of about 35,000, and from 30 to 250 millimolar sodium ions.

Another aspect of the present invention relates to an aqueous solution for the preservation of tissues and organs comprising calcium ions, polyethylene glycol having a molecular weight of about 35,000, from 30 to 250 millimolar sodium ions, and wherein the polyethylene glycol is substantially free of polyethylene glycol having a molecular weight below 15,000.

An additional or alternative aspect of the present invention relates to an aqueous solution for the preservation of tissues and organs comprising calcium ions, polyethylene glycol having a molecular weight of about 35,000, and wherein the concentration of sodium ions is 125 millimolar.

A further aspect of the present invention relates to an aqueous solution for the preservation of tissues and organs comprising from 0.1 to 2 millimolar calcium ions, polyethylene glycol having a molecular weight of about 35,000, and from 30 to 250 millimolar sodium ions.

Another aspect of the present invention relates to an aqueous solution for the preservation of tissues and organs comprising calcium ions, polyethylene glycol having a molecular weight of about 35,000, from 30 to 250 millimolar sodium ions, and from 0.01 to 5 millimolar polyethylene glycol.

An alternative aspect of the present invention relates to an aqueous solution for the preservation of tissues and organs comprising calcium ions, polyethylene glycol having a molecular weight of about 35,000, from 30 to 250 millimolar sodium ions, impermeant anion, a sugar, a membrane-stabilizing agent, a buffer solution, an anti-free radical agent, and an energy source.

A further aspect of the present invention relates to an aqueous solution for the preservation of tissues and organs comprising polyethylene glycol having a molecular weight of about 35,000 and wherein the polyethylene glycol is substantially free of polyethylene glycol having a molecular weight below 15,000, the concentration of sodium ions is from 30 to 250 millimolar, the concentration of calcium ions is from 0.1 to 2 millimolar, and the concentration of polyethylene glycol is from 0.01 to 5 millimolar.

Another aspect of the present invention relates to an aqueous solution for the preservation of tissues and organs comprising polyethylene glycol having a molecular weight of about 35,000 and wherein the polyethylene glycol is substantially free of polyethylene glycol having a molecular weight below 15,000, the concentration of sodium ions is from 30 to 250 millimolar, the concentration of calcium ions is from 0.1 to 2 millimolar, the concentration of polyethylene glycol is from 0.01 to 5 millimolar, the pH of the aqueous solution is from 6.5 to 8, the osmolarity of the aqueous solution is from 290 to 320 millimoles/kg, and the aqueous solution additionally comprises raffinose, $MgSO_4$, $H_2PO_4^-$, glutathione, adenosine, allopurinol, and potassium ions.

Another aspect of the present invention relates to an aqueous solution for the preservation of tissues and organs comprising polyethylene glycol having a molecular weight of about 35,000 and wherein the polyethylene glycol is substantially free of polyethylene glycol having a molecular weight below 15,000, the concentration of sodium ions is from 30 to 250 millimolar, the concentration of calcium ions is from 0.1 to 2 millimolar, the concentration of polyethylene glycol is from 0.01 to 5 millimolar, the pH of the aqueous solution is from 6.5 to 8, the osmolarity of the aqueous solution is from 290 to 320 millimoles/kg, and the aqueous solution additionally comprises raffinose, $MgSO_4$, $H_2PO_4^-$ glutathione, adenosine, allopurinol, potassium ions, and lactobionic acid.

Generally, the concentration of raffinose may be from 20 to 40 millimolar, the concentration of $MgSO_4$ may be from 1 to 10 millimolar, the concentration of $H_2PO_4^-$ may be from 10 to 40 millimolar, the concentration of glutathione may be from 1 to 6 millimolar, the concentration of adenosine may be from 1 to 10 millimolar, the concentration of allopurinol may be from 0.5 to 5 millimolar, the concentration of potassium ions may be from 10 to 40 millimolar, and the concentration of lactobionic acid may be from 70 to 140 millimolar.

More preferably, the concentration of raffinose is 30 millimolar, the concentration of $MgSO_4$ is 5 millimolar, the concentration of $H_2PO_4^-$ is 25 millimolar, the concentration of glutathione is 3 millimolar, the concentration of adenosine is 5 millimolar, the concentration of allopurinol is 1.0 millimolar, the concentration of potassium ions is 25 millimolar, the concentration of sodium ions is 125 millimolar, the concentration of calcium ions is 0.5 millimolar, and the concentration of polyethylene glycol is 0.03 millimolar.

An alternative or additional aspect of the present invention relates to a method for preserving tissues and organs comprising maintaining organs or tissues in a therapeutically effective amount of the aqueous solution described and claimed herein.

A further aspect of the invention relates to a method of maintaining the aqueous solution described and claimed herein at a temperature from 2 to 10° C. More preferably the temperature is about 4° C.

DETAILED DESCRIPTION OF THE INVENTION

The present invention is further described and illustrated by the following examples, which is provided for informational purposes and is not to be construed as limiting.

EXAMPLE I

An aqueous preservation solution of the subject invention was prepared whose composition is reproduced in Table 2:

TABLE 2

| | Concentration (mM) |
|---|---|
| Raffinose | 30 |
| Lactobionate | 100 |
| Reduced glutathione | 3 |
| Adenosine | 5 |
| Allopurinol | 1 |
| PEG (35 000) manufactured by MERCK | 0.029 |
| $MgSO_4 \cdot 7H_2O$ | 5 |
| $H_2PO_4^-$ (provided by $KH_2PO_4$) | 25 |
| $CaCl_2 \cdot 2H_2O$ | 0.5 |
| $Na^+$ (provided by NaOH) | 125 |
| $K^+$ (provided by $KH_2PO_4$) | 25 |

The aqueous solution is prepared by dissolving all of the constituents in an aqueous solution and adjusting the pH of the solution to 7.4 by addition of NaOH.

EXAMPLE II

The performance of the aqueous solution of the subject invention was compared with the BELZER-VIASPAN solution marketed by DUPONT on the kidney and liver.

Trials were carried out on organs isolated and perfused according to known techniques. These techniques consist in the complete isolation ex vivo of the organ and its perfusion with an artificial solution of the KREPS Henseleit-bicarbonate type, enriched with a high-energy substrate and containing albumin.

There were three groups used in this example as set forth below:

Group A: control group directly perfused with the artificial solution without prior preservation;

Group B: organ preserved for a period of ischemia of 24 hours at a temperature of 4° C. in a BELZER-VIASPAN preservation solution before reperfusion with the artificial solution;

Group C: organ preserved for a period of 24 hours of ischemia at a temperature of 4° C. in the aqueous solution of the subject invention.

I/Hepatic Preservation

To assess the efficacy of the preservation solution of the invention on hepatic preservation, the following parameters were studied:

a) Functional parameters

1—Variation of the biliary ouput

The biliary output after transplant is an indicator of good liver function. The biliary outputs were calculated after a period of hypothermic preservation of 24 hours.

The results are presented in Table 3.

TABLE 3

| Biliary output (µl/min/g) | | | |
|---|---|---|---|
| | A | B | C |
| Mean 30 min | 0.51 | 0.17 | 0.35 |
| Mean 60 min | 0.48 | 0.35 | 0.47 |
| Mean 90 min | 0.45 | 0.30 | 0.44 |
| Mean 1200 min | 0.51 | 0.26 | 0.56 |

For Group A, the biliary output was stable during the two hours of perfusion. For Group C, the biliary output was minimal for the first 30 minutes of perfusion, then increased to reach a maximum after 60 minutes and remained stable during the second hour of perfusion.

It was observed that the liver preserved in the solution of the subject invention (Group C) had the highest biliary output (0.56).

2—Excretion of indocyanine green in the bile

Indocyanine green becomes distributed in the vascular volume by rapidly binding to the plasma proteins. It is specifically removed by the liver and concentrated in the bile. The presence of indocyanine green in the liver depends on the rate of perfusion, and its excretion depends on the energy status of the hepatocytes. This parameter not only gives information on the integrity of the endothelial cells, but also information on the integrity of the hepatocytes The percentage excretion of indocyanine green in the bile is represented in Table 4.

TABLE 4

| Excretion of indocyanine green in the bile (%) | | | |
|---|---|---|---|
| | A | B | C |
| Mean | 41 | 11 | 29 |

It was observed that the clearance of indocyanine green is lower for the preservation of the liver in the solution of Group B than in the solution of Group C, which therefore provides a significant improvement.

b) Biochemical parameters

1—Variation of transaminase activity

Transaminases (ALAT and ASAT) are intracellular enzymes. Their presence in the perfusate indicates cellular lysis.

The results are presented in Table 5.

TABLE 5

| | A | B | C |
|---|---|---|---|
| ALAT (IU/L) | | | |
| Mean 30 min | 4 | 13 | 9 |
| Mean 60 min | 5 | 18 | 14 |
| Mean 90 min | 9 | 25 | 16 |
| Mean 1200 min | 13 | 31 | 18 |
| ASAT (IU/L) | | | |
| Mean 30 | 34 | 61 | 44 |
| Mean 60 min | 43 | 71 | 59 |
| Mean 90 min | 50 | 86 | 67 |
| Mean 1200 min | 70 | 107 | 73 |

The livers perfused with the solution of Group B (the intracellular type) release more ASAT and ALAT than the livers preserved in the solution of the subject invention of the extracellular type (Group C). Particularly noteworthy is the large decrease in cellular lysis in going from Group B to Group C. Finally, it is observed that there is no difference in cellular lysis between the liver perfused with the solution of Group A compared with the liver perfused with the solution of Group C.

2—Variation in the Activity of Creatine Kinases

Creatine kinase (CK-BB) is an isoenzyme which is found specifically in the endothelial cells. Its release into the perfusion liquid therefore shows a lysis of these cells. During the preservation in cold ischemia, the endothelial cells undergo severe lesions. The loss of viability of the endothelial cells occurs only after perfusion and the cellular death rate depends on the quality of the preservation and therefore of the preservation solution.

The time 0 referenced in Table 6 corresponds to the replacing of the grafts in perfusion. Under these conditions, the liquid recovered is the preservation liquid kept for 24 hours in the liver. The CK-BB activity assayed is therefore a marker of the lesion of the endothelial cells sustained during the period of preservation.

It is noted that the solution of Group C protects the endothelial cells well.

TABLE 6

| | CK (IU/L) | | |
|---|---|---|---|
| | A | B | C |
| Mean T0-CK BB | 32 | 81 | 33 |
| Mean T30-CK BB | 7 | 40 | 34 |
| Mean (CK IU/L/g) CK BB | 0.004 | 0.022 | 0.022 |

II—Preservation of the Kidney

The efficacy of the solution of the subject invention (Group C) in relation to the BELZER-VIASPAN solution (Group B) and EURO COLLINS solution (Group D) were compared.

The following parameters were studied.

a) Variation of the urinary output

The urinary output after transplant indicates good or poor renal function. The results are set forth in Table 7.

TABLE 7

| | Urinary output (µl/min/g)N | | | |
|---|---|---|---|---|
| | A | B | C | D |
| Mean ± and | 55.43 ± 24.04 | 36.03 ± 15.09 | 118.25 ± 60.99 | 24.61 ± 21.04 |

As shown in Table 7, the urinary output of the kidneys perfused with the solution of Group A remains lower than the urinary output of the kidneys without prior preservation.

In contrast, the kidneys preserved in the solution of the invention have the highest output.

b) Clearance of inulin

This parameter makes it possible to measure the glomerular function of the kidney and gives information on the glomerular filtration rate.

The results are set forth in Table 8.

TABLE 8

| | Clearance of inulin ($\mu$l/min/g) | | | |
|---|---|---|---|---|
| | A | B | C | D |
| Mean ± and | 512.43 ± 109.8 | 49.42 ± 29.21 | 306.90 ± 131.33 | 25.06 ± 24.71 |

As shown in Table 8, the clearance of inulin is low with the preservation of the graft in the solution of Group B. In contrast, the solution of Group C exhibits a significant improvement.

c) Reabsorption of sodium

The rate of reabsorption of sodium makes it possible to measure the renal tubular function. The results are set forth in Table 9.

TABLE 9

| | Rate of reabsorption of sodium (%) | | | |
|---|---|---|---|---|
| | A | B | C | D |
| Mean ± and | 92.2 ± 3.51 | 26.68 ± 12.98 | 61.17 ± 15.18 | 3.3 ± 4.47 |

As shown in Table 9, the reabsorption of sodium is lower for the kidneys preserved in the solution of Group B than for the kidneys preserved in the solution of Group C.

The performance of the biochemical and functional parameters of the perfused organs and tissues is improved when using the aqueous solution of the subject invention when compared with the preservation solutions currently available. Further the extracellular-type solution of the subject invention preserves the heart, tissues, and other organs, including those organs such as the kidney and the liver that are generally only preserved in intracellular-type solutions. Moreover the presence of calcium in the extracellular solution may preserve not only the heart, but also other organs such as the liver and the kidney, for which calcium was thus far absent.

What is claimed is:

1. An aqueous solution for the preservation of tissues and organs comprising:

(a) calcium ions;
    (b) polyethylene glycol having a molecular weight of about 35,000; and
    (c) from 30 to 250 millimolar sodium ions.

2. The aqueous solution of claim 1 wherein said polyethylene glycol is substantially free of polyethylene glycol having a molecular weight below 15,000.

3. The aqueous solution of claim 1 wherein the concentration of sodium ions is 125 millimolar.

4. The aqueous solution of claim 1 wherein the concentration of said calcium ions is from 0.1 to 2 millimolar.

5. The aqueous solution of claim 1 wherein the concentration of said polyethylene glycol is from 0.01 to 5 millimolar.

6. The aqueous solution of claim 1 additionally comprising (a) impermeant anion;
    (b) a sugar;
    (c) a membrane-stabilizing agent;
    (d) a buffer solution;
    (e) an anti-free radical agent; and
    (f) an energy source.

7. The aqueous solution of claim 1 wherein said polyethylene glycol is substantially free of polyethylene glycol having a molecular weight below 15,000, wherein the concentration of said calcium ions is from 0.1 to 2 millimolar, and wherein the concentration of said polyethylene glycol is from 0.01 to 5 millimolar.

8. The aqueous solution of claim 1 having a pH from 6.5 to 8 and an osmolarity from 290 to 320 millimoles/kg and additionally comprising (a) raffinose;
    (b) $MgSO_4$;
    (c) $H_2PO_4^-$;
    (d) glutathione;
    (e) adenosine;
    (f) allopurinol; and
    (g) potassium ions.

9. The aqueous solution of claim 8 additionally comprising lactobionic acid.

10. The aqueous solution of claim 9 wherein the concentration of said raffinose is from 20 to 40 millimolar, the concentration of said $MgSO_4$ is from 1 to 10 millimolar, the concentration of said $H_2PO_4^-$ is from 10 to 40 millimolar, wherein the concentration of said glutathione is from 1 to 6 millimolar, wherein the concentration of said adenosine is from 1 to 10 millimolar, wherein the concentration of said allopurinol is from 0.5 to 5 millimolar, wherein the concentration of said potassium ions is from 10 to 40 millimolar, and wherein the concentration of said lactobionic acid is from 70 to 140 millimolar.

11. The aqueous solution of claim 8 wherein the concentration of said raffinose is 30 millimolar, the concentration of said $MgSO_4$ is 5 millimolar, the concentration of said $H_2PO_4^-$ is 25 millimolar, wherein the concentration of said glutathione is 3 millimolar, wherein the concentration of said adenosine is 5 millimolar, wherein the concentration of said allopurinol is 1.0 millimolar, wherein the concentration of said potassium ions is 25 millimolar, wherein the concentration of said sodium ions is 125 millimolar, wherein the concentration of said calcium ions is 0.5 millimolar, and wherein the concentration of said polyethylene glycol is 0.03 millimolar.

12. A method for preserving tissues and organs comprising maintaining said organs or tissues in the aqueous solution of claim 1.

13. A method for preserving tissues and organs comprising maintaining said organs or tissues in the aqueous solution of claim 10.

14. The method of claim 12 wherein the aqueous solution is maintained at a temperature from 2 to 10° C.

15. The method of claim 13 wherein the aqueous solution is maintained at a temperature from 2 to 10° C.

* * * * *